United States Patent [19]

Friese et al.

[11] Patent Number: 4,903,362
[45] Date of Patent: Feb. 27, 1990

[54] SULFITED FATS AS OILING AGENTS FOR LEATHER AND SKINS

[75] Inventors: Hans-Herbert Friese, Monheim; Friedrich Pieper, Langenfeld-Richrath; Reinhard Bosse, Duessledorf, all of Fed. Rep. of Germany

[73] Assignee: Henkel Kommanditgesellschaft auf Aktien, Dusseldorf, Fed. Rep. of Germany

[21] Appl. No.: 255,909

[22] Filed: Oct. 11, 1988

Related U.S. Application Data

[62] Division of Ser. No. 53,998, May 26, 1987, Pat. No.

[30] Foreign Application Priority Data

May 26, 1986 [DE] Fed. Rep. of Germany ....... 3617691

[51] Int. Cl.$^4$ .................. C14C 5/00; C07C 143/90
[52] U.S. Cl. .................................. 8/94.23; 260/400; 8/94.21; 8/94.22
[58] Field of Search ................... 8/94.22, 94.21, 94.23; 260/400

[56] References Cited

U.S. PATENT DOCUMENTS 4,800,045  1/1989  Friese et al. ...................... 260/400

FOREIGN PATENT DOCUMENTS 3437443  4/1986  Fed. Rep. of Germany .

Primary Examiner—Paul Lieberman
Assistant Examiner—John F. McNally
Attorney, Agent, or Firm—Ernest G. Szoke; Wayne C. Jaeschke; Henry E. Millson, Jr.

[57] ABSTRACT

Sulfited fats prepared by oxidation of fats with oxygen-containing gas mixtures and simultaneous or subsequent sulfitation using alkali and/or ammonium hydrogen sulfites, wherein the fats used are mixtures containing (A) fats having iodine numbers below about 100 and
(B) fatty acid esters having iodine numbers of from about 60 to about 100 and containing from 12 to 24 carbon atoms in the linear or branched, natural and/or synthetic fatty acid residue and from 1 to 5 carbon atoms in the monofunctional alcohol residue the ratio by weight of (A) to (B) being from about 9:1 to about 1:4.

11 Claims, No Drawings

SULFITED FATS AS OILING AGENTS FOR LEATHER AND SKINS

This application is a division of application Ser. No. 053,998, filed May 26, 1987, now Pat. No. 4,800,045.

BACKGROUND OF THE INVENTION

1. Field of the Invention

This invention relates to sulfited fats prepared from difficultly sulfitable fats having iodine numbers below 100, to their use as oiling agents for leather and skins and to a process for sulfiting fats having iodine numbers below 100.

2. Statement of Related Art

Sulfited fats used as oiling agents for leather and skins are produced by oxidation of fats with oxygen-containing gas mixtures, for example air, and simultaneous or subsequent sulfitation with alkali and/or ammonium hydrogen sulfite. For fats to be sulfited at all, it is absolutely essential to oxidize them before or during sulfitation by introduction of oxygen-containing gas mixtures. However, since the oxidizability of fats decreases with decreasing iodine number, relatively highly unsaturated fats and oils, i.e. those having iodine numbers above about 100 and preferably above about 130, are normally used (cf. for example "Rauchwarenherstellung und Pelzkonfektion", VEB Fachbuchverlag Leipzig 1970, page 116).

Sulfited fats prepared from sea-animal oils having high iodine numbers, for example whale oil or fish oil, or from vegetable oils having high iodine numbers, for example soya oil, form readily water-emulsifiable substances of high emulsion stability which are particularly suitable for oiling leather and skins. If, by contrast, difficultly sulfitable fats having an iodine number below 100, for example sperm oil, are subjected to oxidizing sulfitation, the oxidation velocity of the fats decreases drastically and products difficult to emulsify in water and having poor emulsion stability are obtained. In order nevertheless to be able to use these sulfitation products for oiling leather and skins, they have to be mixed with emulsifiers or with water-emulsifiable fats which are capable of co-emulsifying the difficulty emulsifiable sulfitation products.

STATEMENT OF THE INVENTION

Other than in the operating examples, or where otherwise indicated, all numbers expressing quantities of ingredients or reaction conditions used herein are to be understood as modified in all instances by the term "about".

An object of the present invention is to provide sulfited fats prepared from difficultly sulfitable fats having iodine numbers below 100 which form readily water-emulsifiable products of high emulsion stability and which are suitable for oiling leather and skins.

It has now surprisingly been found that difficultly sulfitable fats having iodine numbers below 100, for example coconut oil, palm kernel oil, palm oil, tallow, lard, neat's-foot oil, sperm oil, whale oil, triolein, oleic acid, wax esters, fatty acid monoglycerides, fatty acid diglycerides, and/or fatty acid triglycerides, form readily water-emulsifiable sulfitation products of high emulsion stability providing they are mixed before the oxidizing sulfitation step with fatty acid esters having iodine numbers of from 60 to 100 in a ratio by weight of fat to ester of from 9:1 to 1:4. Suitable fatty acid esters contain from 12 to 24 carbon atoms in the fatty acid residue, which is of natural and/or synthetic origin and which may be linear or branched, and from 1 to 5 carbon atoms in the monofunctional alcohol residue. Fatty acid esters containing unsaturated fatty acid residues can be used either individually or in combination with fatty acid esters containing saturated fatty acid residues.

Accordingly, the present invention relates to sulfited fats prepared by oxidation of fats with oxygen-containing gas mixtures and simultaneous or subsequent sulfitation using alkali and/or ammonium hydrogen sulfites, wherein the fats used are mixtures containing (A) fats having iodine numbers below about 100, and
(B) fatty acid esters having iodine numbers from 60 to 100 and containing from 12 to 24 carbon atoms in the linear or branched, natural and/or synthetic fatty acid residue and from 1 to 5 carbon atoms in the monofunctional alcohol residue;

the ratio of weight of A to B being from 9:1 to 1:4.

Difficultly sulfitable fats having iodine numbers below 100, and preferably of from 7 to 95, are preferably mixed with fatty acid esters having iodine numbers of from 60 to 100 in a ratio by weight of fat to fatty acid ester of from 4:1 to 2:3.

The difficultly sulfitable fats having iodine numbers below 100 include, for example, fats and oils containing unsaturated fatty acids and/or fatty acid esters, natural and/or synthetic unsaturated fatty acids containing from 12 to 24 carbon atoms, if desired in combination with natural and/or synthetic saturated fatty acids containing from 12 to 24 carbon atoms, natural and/or synthetic unsaturated fatty acid esters containing from 12 to 24 carbon atoms both in the fatty acid residue and in the alcohol residue, if desired in combination with the analogous natural and/or synthetic saturated fatty acid esters, synthetic fatty acid monoglycerides prepared from unsaturated fatty acids containing from 12 to 24 carbon atoms, if desired in combination with the analogous saturated, synthetic fatty acid monoglycerides, synthetic fatty acid diglycerides and triglycerides prepared from unsaturated or unsaturated/saturated fatty acids containing from 12 to 24 carbon atoms and mixtures of fats from the above-mentioned groups. The preferred difficultly sulfitable fats having iodine numbers below 100 and preferably of from 7 to 95 include coconut oil, palm kernel oil, palm oil, tallow, lard, neat's-foot oil, sperm oil, whale oil, triolein. oleic acid, wax esters, fatty acid monoglycerides, fatty acid diglycerides, fatty acid triglycerides, and mixtures thereof.

The difficultly sulfitable fats having iodine numbers below 100 and preferably of from 7 to 95 are preferably mixed with fatty acid esters having iodine numbers of from 70 to 85. It is possible to use both unsaturated fatty acid esters and also mixtures of unsaturated and saturated fatty acid esters having iodine numbers of from 60 to 100 and preferably of from 70 to 85.

Suitable fatty acid esters having iodine numbers of from 60 to 100 and preferably of from 70 to 85 contain from 12 to 24, preferably from 12 to 18, and more preferably from 16 to 18 carbon atoms in the fatty acid residue and from 1 to 5 carbon atoms in the monofunctional alcohol residue. The fatty acid residue may be linear or branched. Fatty acid methyl, ethyl, isopropyl, and/or isobutyl esters are preferably used as the fatty acid esters.

Fat mixtures containing difficultly sulfitable fats having iodine numbers below 100 and preferably of from 7 to 95, and fatty acid esters having iodine numbers of from 60 to 100, and preferably of from 70 to 85, are sulfited with 0.5 to 2.5 moles of alkali and/or ammonium hydrogen sulfites or alkali and/or ammonium hydrogen sulfites and alkali and/or ammonium sulfites in the form of aqueous solutions or suspensions, preferably in the form of saturated aqueous solutions, at temperatures of from 70° to 110° C., and preferably at temperatures of from 85° to 95° C.

The present invention also relates to the use of the sulfited fats according to the invention, if desired in combination with other oiling agents known per se and/or with anionic and/or nonionic emulsifiers, as oiling agents for leather and skins.

Suitable oiling agents which may be used together with the sulfited fats according to the invention are, for example, sulfated fats, sulfonated fats, sulfited fats prepared from high-iodine fats, sulfochlorinated fats or phosphated fats, neutral oils, and mixtures thereof.

Suitable anionic and/or nonionic emulsifiers are, for example, alkylene oxide adducts of fatty alcohols, fatty acids, fatty acid amides, fatty amines, and/or alkyl phenols and sulfuric acid and/or phosphoric acid esters thereof, fatty alcohol sulfates, alkyl sulfates and/or alkylbenzene sulfonates.

Oiling agents containing sulfited fats according to the invention are used in quantities of from 1 to 20% by weight, based on the pelt or sharing weight, and preferably in quantity of from 1 to 2% by weight during chrome tanning, and in quantities of from 4 to 16% by weight during the main tanning process or, depending on the type of leather or skin, in concentrations of from 2 to 10 g/l liquor and preferably in concentrations of from 5 to 7 g/l liquor. In oiling agents consisting of several oiling agents and, optionally, emulsifiers, the sulfited fats according to the invention are present in a quantity of from 10 to 95% by weight.

The oiling temperature is in the range of from 20° to 75° C. and preferably in the range of from 35° to 50° C.

The present invention also relates to a process for sulfiting fats having iodine numbers below about 100, characterized in that (A) fats having iodine numbers below about 100 are mixed with (B) fatty acid esters having iodine numbers of from about 60 to about 100 and containing from 12 to 24 carbon atoms in the linear or branched, natural and/or synthetic fatty acid residue and from 1 to 5 carbon atoms in the monofunctional alcohol residue, the ratio by weight of (A) to (B) being from about 9:1 to about 1:4, and the resulting fatty mixtures are oxidized in known manner with oxygen-containing gas mixtures and then sulfited using alkali and/or ammonium hydrogen sulfites, if desired while more oxygen-containing gas mixture is passed through.

It is preferred to use sulfite fat mixtures containing fats having iodine numbers below about 100 and preferably of from 7 to 95 and fatty acid esters having iodine numbers of from 60 to 100 in a ratio by weight of from 4:1 to 2:3.

The difficultly sulfitable fats having iodine numbers below 100, which are suitable as adducts for the process according to the invention for sulfiting fats having iodine numbers below 100, are those described above.

According to the invention, the difficultly sulfitable fats having iodine numbers below 100 and preferably of from 7 to 95 are mixed before the oxidizing sulfitation with fatty acid esters having iodine numbers of from 60 to 100 and preferably of from 70 to 85 in a ratio by weight of fat to fatty acid ester of from 9:1 to 1:4 and preferably of from 4:1 to 2:3. Suitable fatty acid esters having iodine numbers of from 60 to 100 and preferably of form 70 to 85 contain from 12 to 24, preferably from 12 to 18 and more preferably from 16 to 18 carbon atoms in the fatty acid residue and from 1 to 5 carbon atoms in the monofunctional alcohol residue. The fatty acid residue may be linear or branched. It is possible to use both unsaturated fatty acid esters and also mixtures of saturated and unsaturated fatty acid esters. The fatty acid esters can be prepared by various methods, for example by transesterification of fats and oils with monofunctional alcohols containing from 1 to 5 carbon atoms or by esterification of fatty acids of natural and/or synthetic origin with monofunctional alcohols containing from 1 to 5 carbon atoms. Methanol, ethanol, isopropanol and/or isobutanol are preferably used as alcohol components for the preparation of fatty acid esters.

In the process of the invention for sulfiting fats having iodine numbers below 100, the fat mixtures are oxidized at 70° to 200° C., and preferably at 80° to 120° C. by passing an oxygen-containing fat mixture through the fats, which are then sulfited, optionally while more oxygen-containing gas mixture is passed through, at 70° to 110° C. and preferably at 85° to 95° C. with 0.5 to 2.5 moles of alkali and/or ammonium hydrogen sulfites or alkali and/or ammonium hydrogen sulfites and alkali and/or ammonium sulfites/kg fat mixture used in the form of an aqueous solution or suspension, preferably in the form of a saturated aqueous solution. Sulfitation is preferably carried out with 0.5 to 2 moles alkali and/or ammonium hydrogen sulfites or in admixture with alkali and/or ammonium sulfites/kg fat mixture used.

The sulfiting agents are mixed with the oxidized fat mixtures by adding the sulfiting agent in the form of an aqueous solution or suspension and preferably in the form of a saturated aqueous solution to the oxidized fat mixture or by stirring the oxidized fat mixture into an aqueous solution or suspension and preferably into a saturated aqueous solution of the sulfiting agent.

The sulfited fats according to the invention are distinguished by high water emulsifiability with excellent emulsion stability. They are therefore particularly suitable for oiling leather and skins.

Compared with sulfitation products prepared from high-iodine fats, for example fish oil, the sulfitation products according to the invention show distinctly better light stability. Thus, the light fastness of leathers, as measured in accordance with DIN 54 004, oiled with fish oil sulfite reaches stage 1 of the 8-stage cotton blue scale while leathers treated with the sulfited fats according to the invention reach stage 4 or stage 5. On the scale in question, stage 1 signifies very poor light stability and stage 8 very high light stability.

The invention will be illustrated but not limited by the following examples.

EXAMPLES

I.no.=iodine number, AS=active substance, mins.-=minutes, h.=hours.

Unless otherwise stated, "%" means "% by weight" while "g/l" means "g/l liquor".

Example 1

600 g tallow (I.no. 52) were mixed with 400 g $C_{16}$–$C_{18}$ fatty acid methylester (I.no. 80). The resulting mixture was oxidized at 90° C. by passing air through, and was then sulfited at 95° C. with 1.5 moles sodium hydrogen sulfite per kg fat mixture used in the form of an aqueous 40% by weight sodium hydrogen sulfite solution. On completion of sulfitation, the product was cooled to room temperature.

Example 2

500 g palm kernel oil (I.no. 17) were mixed with 500 g. $C_{16}$–$C_{18}$ fatty acid methylester (I.no. 80), oxidized at 110° C. by passing air through and then sulfited at 95° C. with a mixture containing 1.2 moles sodium hydrogen sulfite and 0.6 mole sodium sulfite/kg fat mixture used in the form of a saturated aqueous solution. On completion of sulfitation, the product was cooled to room temperature.

Example 3

700 g filtered lard (I.no. 87) were mixed with 300 g $C_{12}$–$C_{18}$ fatty acid methylester (I.no. 78), oxidized at 85° C. by passing air through and then sulfited at 90° C. with 1.3 moles sodium hydrogen sulfite/kg fat mixture used in the form of an aqueous, 40% by weight sodium hydrogen sulfite solution. On completion of sulfitation, the product was cooled to room temperature.

Example 4

A mixture of 550 g triolein (I.no. 92) and 450 g $C_{16}$–$C_{18}$ fatty acid methylester (I.no. 88) was subjected to oxidizing sulfitation in the same way as in Example 1.

Example 5

A mixture of 500 g technical oleic acid (I.no. 85) and 500 g $C_{16}$–$C_{18}$ fatty acid isopropylester (I.no. 80) was subjected to oxidizing sulfitation in the same way as in Example 2.

Example 6

600 g technical oleyloleate (I.no 91) were mixed with 400 g $C_{16}$–$C_{18}$ fatty acid methylester (I.no. 85), oxidized at 120° C. by passing air through and then sulfited at 90° C. with 2.0 moles sodium hydrogen sulfite/kg fat mixture used in the form of an aqueous, 40% by weight sodium hydrogen sulfite solution. On completion of sulfitation, the product was cooled to room temperature.

Example 7

A mixture of 700 g neat's-foot oil (I.no 85) and 300 g $C_{16}$–$C_{18}$ fatty acid methylester (I.no. 80) was subjected to oxidizing sulfitation in the same as in Example 2.

Example 8

Chrome-taned leathers were oiled with 7% by weight AS, based on sharing weight, of the sulfited fat mixtures of Examples 1 to 7 and with sulfited fish oil prepared from fish oil (I.no. 135) by oxidation with air at 90° C. and sulfitation at 95° C. with 1.5 moles sodium hydrogen sulfite/kg fish oil in the form of an aqueous, 40% by weight sodium hydrogen sulfite solution. After finishing in the usual way, the leathers are tested for their fastness to light in accordance with DIN 54 004. The higher the light stability of the oiling agents, the higher the stage number on the 8-stage cotton blue scale. Table 1 shows the results of the individual measurements.

TABLE 1

| Oiling agent | Fastness to light (as measured in accordance with DIN 54 004) |
| --- | --- |
| Example 1 | stage 5 |
| Example 2 | stage 5 |
| Example 3 | stage 4 |
| Example 4 | stage 4 |
| Example 5 | stage 4 |
| Example 6 | stage 4 |
| Example 7 | stage 4 |
| Sulfited fish oil | stage 1 |

APPLICATION EXAMPLE A

Use during chrome tanning.
All quantities based on pelt weight.
Starting material: pelts of South-German origin.

| | | |
| --- | --- | --- |
| Pickling: | 100% water 25° C. | |
| | 8% sodium chloride | 10 mins. |
| | 0.6% formic acid (85%) diluted 1:10 | 15 mins. |
| | 0.7% sulfuric acid (98%) diluted 1:10 | 3 h. |
| | pH ca. 3.5 | |
| Tanning and oiling: | 2% AS containing 95 parts by weight sulfitate, prepared from 60% lard, I.no. 80 and 40% $C_{12}$–$C_{24}$ fatty acid methylester, I.no. 85 and 5 parts by weight $C_{16}$–$C_{18}$ fatty alcohol polyglycolether | 30 mins. |
| | 8% commerical chrome tanning agent containing 25% $Cr_2O_3$, 33% basic basification with 0.5% MgO pH 3.7–3.8 sharing, retanning, reoiling in the usual way. | 30 mins. 7 h. |

APPLICATION EXAMPLE B

Oiling of upper leathers.
All quantities based on sharing weight.
Starting material: hide wet blue, sharing thickness 1.7 mm.

| | | |
| --- | --- | --- |
| Washing: | 200% water 40° C. fresh liquor | 10 mins. |
| Neutralization | 100% water 40° C. 0.5% sodium formate Rinsing with water at 60° C. | 30 mins. |
| Retanning | 100% water 60° C. | |
| | 0.5% commercial neutralizing tanning agent | 15 mins. |
| | 4% commercial resin tanning agent | 30 mins. |
| | 3% commercial synthetic full tanning agent | 40 mins. |
| Oiling: | 3% AS sulfitate prepared from 50% triolein, I.no. 86 and 50% fatty acid isopropylester, I.no. 80 | 45 mins. |
| | 3% AS commercial fish oil sulfate | |
| | 0.5% AS $C_{16}$–$C_{18}$ alkyl sulfate | |
| | 0.5% formic acid (85%) diluted 1:10 | 15 mins. |
| | hoard up leather and | |

| | -continued | |
|---|---|---|
| | finish in the usual way. | |

APPLICATION EXAMPLE C

Oiling of apparel leather.
All quantities based on sharing weight.
Starting material: hide wet blue, sharing thickness 0.8 mm.

| | | |
|---|---|---|
| Washing: | 200% water 40° C. fresh liquor | 10 mins. |
| Chrome retanning: | 100% water 40° C. 3% commercial chrome tanning agent containing 25% $Cr_2O_3$, 33% basic 3% commercial synthetic full tanning agent 1.5% sodium aluminium silicate | 15 mins. |
| Oiling: | 3% AS sulfitate, prepared from 45% lard, I.no. 85, 45% fatty acid methylester, I.no. 80, 10% glycerol monooleate, I.no. 75, 0.2% AS tallow alcohol polyglycolether 1% AS $C_{12}$–$C_{18}$ alkylsulfate | 45 mins. |
| Neutralization: | 2% sodium hydrogen carbonate rinsing 60° C. dyeing, retanning, reoiling and finishing in the usual way. | 60 mins. |

APPLICATION EXAMPLE D

Oiling of sheepskin suede.
Starting material: pickled sheepskins
Liquor ratio: 1:20
Chrome tanning: bath temperature 35° C.

| | | |
|---|---|---|
| Tanning and oiling | 40 g/l sodium chloride 0.5 g/l AS $C_{12}$–$C_{18}$ alkyl sulfate 4 g/l AS sulfitate, prepared from 60% technical oleyloleate, I.no. 84, 40% $C_{12}$–$C_{24}$ fatty acid methylester, I.no. 72 0.5 g/l AS $C_{16}$–$C_{18}$ fatty alcohol polyglycolether | 30 mins. |
| | 4 g/l commercial chrome tanning agent containing 25% $Cr_3O_3$, 33% basic | 30 mins. |
| | 4 g/l commercial chrome tanning agent | 30 mins. |
| | 4 g/l commercial chrome tanning agent move liquor back and forth | 5 h. |
| | 1 g/l sodium hydrogen carbonate | overnight |
| | 1 g/l sodium hydrogen carbonate pH 3.8–3.9 | 4 h. |

| -continued | |
|---|---|
| then hoard up leather and finish in the usual way. | |

I claim:

1. An oiling agent for the treatment of leather and skins comprising
   I. from about 10 to about 95% by weight of an oxidized sulfited fat mixture comprising
      A. at least one sulfited fat having an iodine number before sulfitation below about 100; and
      B. at least one sulfited fatty acid ester having an iodine number before sulfitation of from about 60 to about 100, and containing from 12 to 24 carbon atoms in a linear or branched, natural or synthetic fatty acid residue, and wherein the ester residue is from a monofunctional $C_1$–$C_5$ alcohol;
   wherein the ratio by weight of A to B is from about 9:1 to about 1:4; and
   II. one or more of a sulfated fat, a sulfonated fat, a sulfochlorinated fat, a phosphated fat, a neutral oil, an anionic emulsifier, and a nonionic emulsifier.

2. A method for the treatment of leather or skins comprising contacting the leather or skin with the oiling agent of claim 1 at a temperature in the range of from about 20° to about 75° C.

3. An oiling agent according to claim 1 wherein in component I the ratio of A to B is from about 4:1 to about 2:3.

4. An oiling agent according to claim 1 wherein in component IA the iodine number before sulfitation is from about 7 to about 95.

5. An oiling agent according to claim 1 wherein component I A is at least one sulfited fat selected from the group; coconut oil, palm kernel oil, palm oil, tallow, lard, neat's-foot oil, sperm oil, whale oil, triolein, oleic acid, wax esters, fatty acid monoglycerides, fatty acid diglycerides, and fatty acid triglycerides.

6. An oiling agent according to claim 1 wherein in component IB the iodine number before sulfitation is from about 70 to about 85.

7. An oiling agent according to claim 1 wherein in component IB the fatty acid residue contains from 12 to 18 carbon atoms.

8. An oiling agent according to claim 7 wherein the fatty acid residue contains from 16 to 18 carbon atoms.

9. An oiling agent according to claim 1 wherein in component IB the ester is a methyl, ethyl, isopropyl, or isobutyl ester.

10. A method for the treatment of leather or skins comprising contacting the leather or skin with the oiling agent of claim 5 at a temperature in the range of from about 20° to about 75° C.

11. A method for the treatment of leather or skins comprising contacting the leather or skin with the oiling agent of claim 6 at a temperature in the range of from about 20° to about 75° C.

* * * * *